(12) United States Patent
Klenk

(10) Patent No.: US 6,187,097 B1
(45) Date of Patent: Feb. 13, 2001

(54) DEVICE FOR SPRAYING LIQUIDS ONTO CONTAINERS

(75) Inventor: Klaus Klenk, Flensburg (DE)

(73) Assignee: Krones AG (DE)

( * ) Notice: Under 35 U.S.C. 154(b), the term of this patent shall be extended for 0 days.

(21) Appl. No.: 09/063,280

(22) Filed: Apr. 20, 1998

(30) Foreign Application Priority Data

Apr. 23, 1997 (DE) .......................................... 297 07 271 U
Sep. 17, 1997 (DE) .......................................... 297 16 644 U

(51) Int. Cl.$^7$ ...................................................... B05C 7/02
(52) U.S. Cl. .................... 118/315; 118/317; 118/DIG. 3; 422/302; 422/304; 99/362; 99/455; 99/483
(58) Field of Search ............................... 118/DIG. 3, 317, 118/315, 412; 427/421; 422/302, 304; 239/548, 566, 553, 553.5, 590.5, 592; 99/362, 455, 483; 425/461

(56) References Cited

U.S. PATENT DOCUMENTS

| 4,704,958 | 11/1987 | Braymond | ............................... 99/470 |
| 5,264,036 | * 11/1993 | Haas et al. | ............................ 118/315 |
| 5,334,352 | * 8/1994 | Johnson | .................................. 422/99 |
| 5,759,627 | * 6/1998 | Kokubo et al. | ....................... 118/410 |

FOREIGN PATENT DOCUMENTS

| 2142124 | 3/1973 | (DE) . |
| 2907916 | 4/1985 | (DE) . |

* cited by examiner

*Primary Examiner*—Laura Edwards
(74) *Attorney, Agent, or Firm*—Tilton, Fallon, Lungmus & Chestnut

(57) ABSTRACT

A pasteurizing system for spraying liquids onto containers such as bottles and cans has a conveyor for conveying the containers and one or more spray tubes mounted parallel to the conveyor's plane of motion. Each of the spray tubes has outlet openings longitudinally distributed along its bottom side, and the inside cross section of the spray tube decreases along its length from a liquid inlet end of the spray tube, to an opposite end of the spray tube.

10 Claims, 2 Drawing Sheets

DEVICE FOR SPRAYING LIQUIDS ONTO CONTAINERS

DESCRIPTION

Figure 1:
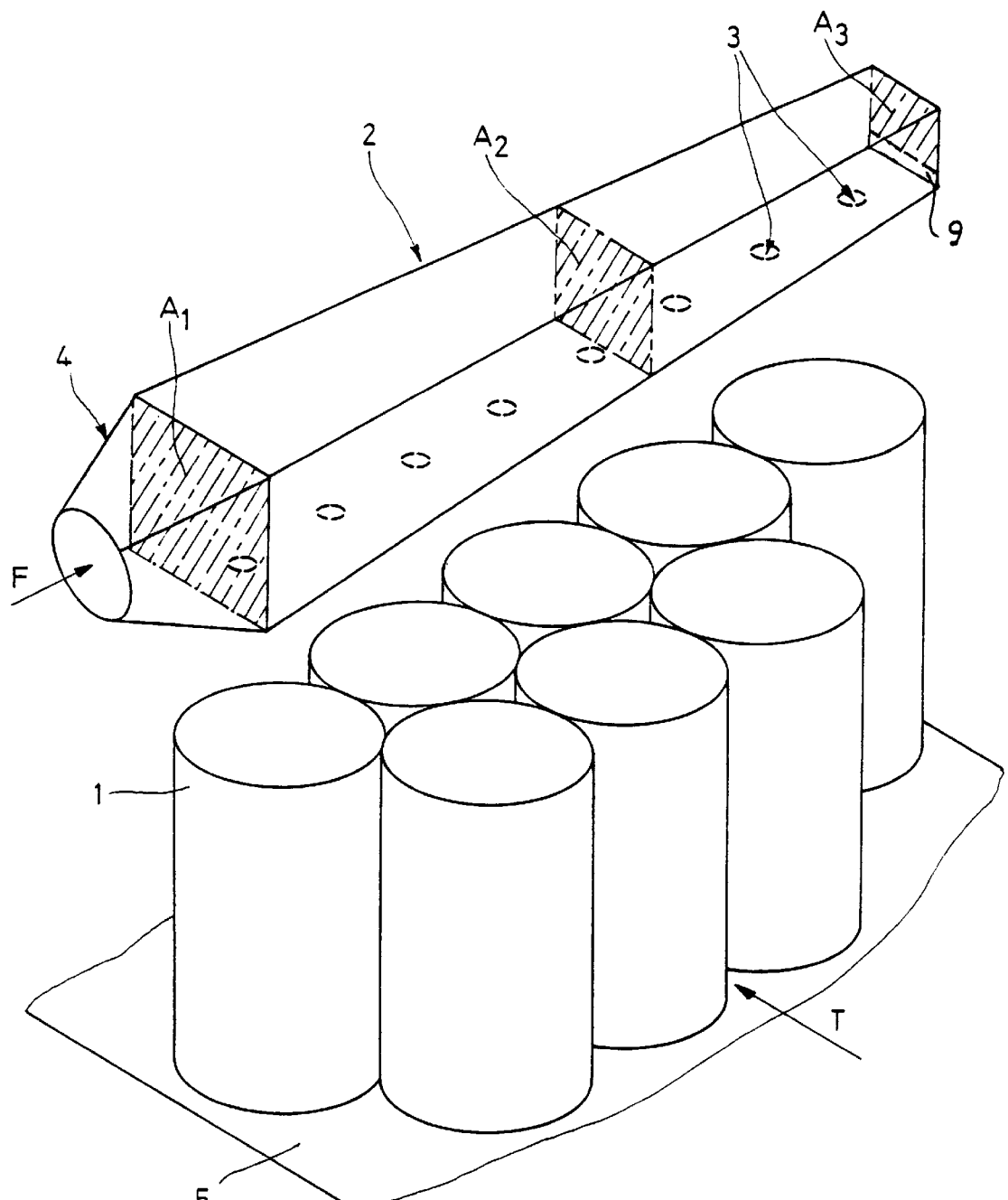

This innovation relates to a device for spraying liquids onto containers by means of at least one spray tube which has a plurality of outlet openings distributed over its longitudinal extent and is supplied through a liquid inlet.

Such devices are used in tunnel pasteurizers, through-coolers or warming installations so that heated or cooled liquid can be made to trickle over cans, bottles, etc. containing foods or beverages. In pasteurizers, a predetermined number of so-called Pasteur units (PE) are to be achieved by a precisely defined energy transfer. If the PE number is too high, it can have a negative effect on the taste of the food, whereas if the PE number is too low, adequate shelf-life is not ensured, i.e., a uniform energy transfer is the goal. The basic design of such machines is known from German Patent 2,142,124 (FIGS. 1 and 2) or U.S. Pat. No. 4,704,958 (FIGS. 1 and 3), for example.

Cooling and heating installations for bottles or cans are necessary when beverages are bottled hot or cold, for example, because otherwise problems can occur in subsequent packaging operations (labeling, film sheathing) due to condensation or the like.

In the aforementioned machines, the containers to be treated are usually conveyed by a conveyor system in multiple lines side by side beneath spray tubes which are oriented with their longitudinal extent across the direction of conveyance and which have a multitude of spray openings or jets along the bottom of the tube. One design of a corresponding spray tube is known from German Patent 2,907,916 C2. The spray tube described in this document has a uniform cross section over its entire length. The spray tube is supplied with liquid through an inlet line from one end in the axial direction. One disadvantage is that the liquid delivery through the individual spray openings which are different distances away from the inlet connection is not uniform due to the unequal quantity distribution and pressure conditions inside the tube.

This innovation is thus based on the object of creating a spray tube with improved delivery.

This object is achieved by an inside cross section of the spray tube which decreases with increasing distance from the liquid inlet. This ensures a uniform delivery of liquid, regardless of the distance of the outlet openings from the inlet connection. The measure of the reduction in inside cross section based on the distance from the inlet connection depends on the spacing between outlet openings, i.e., the number of openings per unit of length, their outlet capacity and optionally also the frictional losses in the tube, and it is designed so that the total pressure prevailing in the spray tube is approximately the same in the area of each outlet opening.

If the outlet openings are distributed at regular intervals along the longitudinal extent of a spray tube and if they all have the same open cross section, a continuous reduction in the inside cross section of the spray tube with increasing distance from the inlet connection is advantageous. Such a spray tube may be provided with an interior that tapers conically or in a wedge or pyramid shape starting from the inlet connection.

If the liquid supply is not over one of the ends of the spray tube but instead in the area in between, then the maximum inside cross section is at the point of the inlet connection, decreasing from there toward the ends of the spray tube. The inside cross section of a spray tube supplied by an inlet line at each end simultaneously would be exactly the opposite. In this case the inside cross section would decrease from the ends of the tube toward the center.

Figure 2:
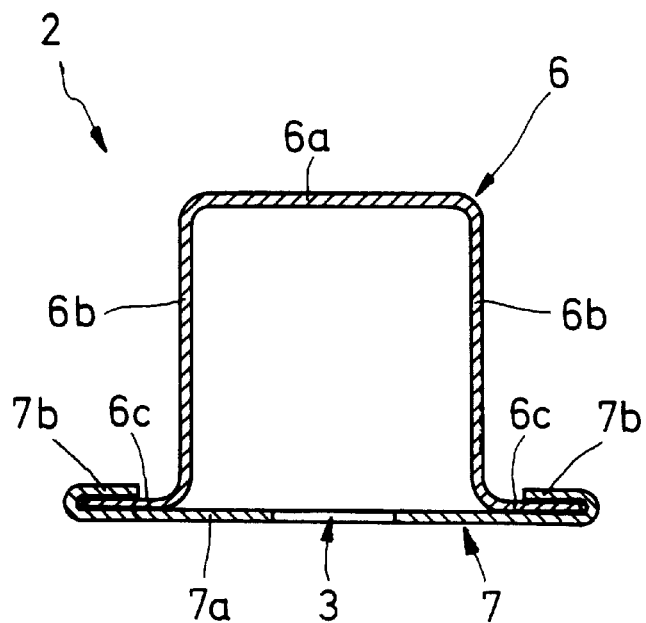

A preferred embodiment of a spray tube is explained below on the basis of the figures, which show the following:

FIG. 1: a perspective view of a spray tube;

FIG. 2: a vertical section through a spray tube and

Figure 3:
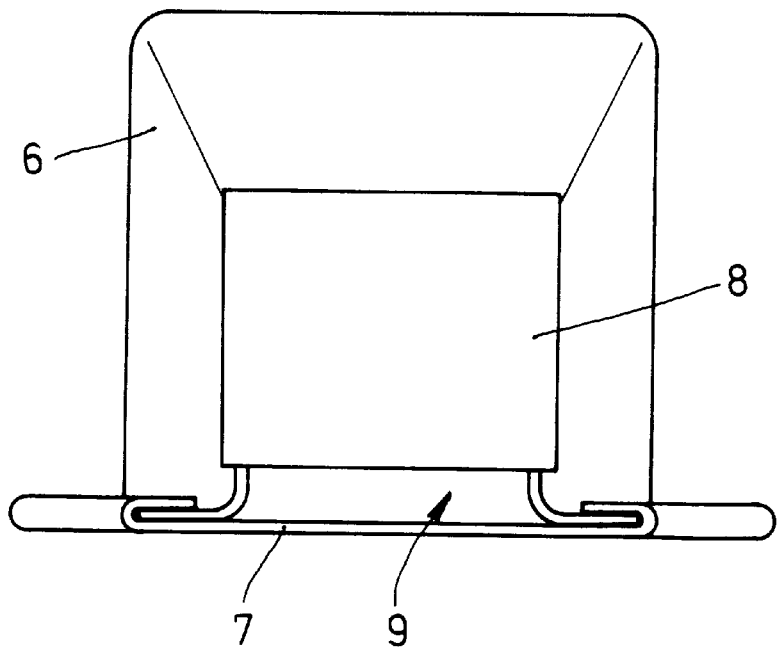

FIG. 3: a view of the end of the spray tube according to FIG. 1 opposite the liquid inlet.

Spray tube 2, which is shown schematically in FIG. 1, is aligned with its longitudinal extent across the direction T of movement of a stream of cans conveyed in multiple lines by a conveyor 5. At regular intervals on the bottom side of spray tube 2 which faces cans 1 there are several outlet openings 3 of the same size. At one end is a connection 4 for the liquid inlet, while the opposite end of the tube is sealed except for a small gap (FIG. 3) to eliminate dirt particles. The liquid is supplied in the direction of arrow F.

The interior of the spray tube has the shape of a truncated pyramid, with the tube end having the largest inside cross-sectional area A1 being provided for liquid inlet 4. Alternatively, the spray tube can have the shape of a wedge or a pyramid. Liquid flows axially outward from this connection 4 into the continuously tapering interior of the tube.

As FIG. 1 also shows, the inside cross-sectional area A1 of spray tube 2 decreases steadily, as seen in the direction of flow F, with increasing distance from the tube end on the connection side in the direction of the opposite end. The reduction in cross section (A1 to A3) is designed so that the total pressure (static and dynamic fluid pressure) in spray tube 2 is approximately the same in the area of each outlet opening 3. This yields a uniform delivery of liquid regardless of the distance of each individual outlet opening 3 from the liquid inlet point 4. Especially when used in tunnel pasteurizers, this property of such spray tubes is extremely important because this advantageously ensures a constant heat transfer, regardless of whether the bottles, cans, etc. which contain foods or beverages are conveyed past the end of the spray tube 2 near the connection or farther away from it. The spray tube according to this innovation can also be used in bottle cleaning machines, where it is also advantageous to have all bottles exposed to the same amount of cleaning agent.

A spray tube with an interior that tapers in the axial direction can be produced by bending a sheet metal part that has already been cut to shape. FIG. 2 shows a design that is especially simple to manufacture. As this shows, spray tube 2 consists of two individual parts 6 and 7 which are joined together, namely a first sheet metal blank 6 having an essentially U-shaped cross section that is open at the bottom due to four non-parallel bending edges, and a second sheet metal blank 7 forming the bottom part of the spray tube. The first sheet metal blank 6 which forms the top part of the spray tube has two side faces 6b which are bent vertically downward from a top side 6a and develop seamlessly into flange faces 6c which project down at a right angle at their lower end. The outlet openings 3 are punched in the main body portion 7a of the second trapezoidal sheet metal blank 7. In the extended form, this sheet metal blank 7 is wider than the U-shaped sheet metal blank 6 in the area of its flange faces 6c, so that the second sheet metal blank 7 can be connected at its flanged longitudinal sides 7b to flange faces 6c by flanging in a form-fitting manner according to the diagram in FIG. 2.

The end face of spray tube 2 opposite the liquid connection 4 (FIG. 1) is provided with a welded plate 8 (FIG. 3) which covers the cross section of the tube except for a narrow gap 9. Foreign bodies can be washed out of the interior of the tube to the outside through gap 9. FIG. 3 also shows that not only do the vertical side faces of the top part 6 converge in a tapering manner from the liquid connection in the direction of plate 8, but also the top side drops relative to the horizontally oriented bottom part 7, i.e., the spray tube has a housing contour resembling a truncated pyramid.

What is claimed is:

1. Device for pasteurizing filled, closed containers, comprising in combination a conveyor for conveying filled, closed containers, at least one spray tube mounted parallel to a plane of said conveyor, said at least one spray tube having a plurality of outlet openings distributed over a longitudinal extent thereof, each of said outlet openings being directed toward the conveyor, said at least one spray tube being supplied with liquid through a liquid inlet, said at least one spray tube having an end opposite the liquid inlet that is sealed except for a gap to eliminate dirt particles, and an inside cross section of said spray tube decreases with increasing distance from said liquid inlet.

2. Device according to claim 1, wherein said inside cross section has a continuous reduction.

3. Device according to claim 1, wherein said liquid inlet (4) is at one end of said spray tube (2) and the opposite end (8) is partially closed.

4. Device according to claim 1, wherein the interior of said spray tube (2) is formed as one of a wedge, pyramid or a truncated pyramid.

5. Device according to claim 1, wherein said spray tube is arranged in a plane parallel to said conveyor and is oriented with its longitudinal extent perpendicular to the direction of conveyance of said conveyor.

6. Device according to claim 1, wherein several said spray tubes are arranged in parallel in said plane parallel to said conveyor.

7. Device for treating containers, comprising in combination a conveyor for conveying containers, at least one spray tube mounted parallel to a plane of said conveyor, said at least one spray tube having a plurality of outlet openings distributed over a longitudinal extent thereof, each of said outlet openings being directed toward the conveyor, said at least one spray tube being supplied with liquid through a liquid inlet, and an inside cross section of said spray tube decreases with increasing distance from said liquid inlet, wherein said spray tube has a housing that tapers in the longitudinal direction and includes a first bent sheet metal blank having two vertical walls, an inclined top wall and a horizontal bottom created by a second flat sheet metal blank being connected to said first bent sheet metal blank in a form-fitting manner.

8. Device for treating containers, comprising in combination a conveyor for conveying containers, at least one spray tube mounted parallel to a plane of said conveyor, said at least one spray tube having a plurality of outlet openings distributed over a longitudinal extent thereof, each of said outlet openings being directed toward the conveyor, said at least one spray tube being supplied with liquid through a liquid inlet, and an inside cross section of said spray tube decreases with increasing distance from said liquid inlet, wherein said spray tube has a housing consisting essentially of two individual parts, said individual parts being sheet metal blanks, and the individual parts are connected in a form-fitting manner.

9. Device according to claim 8, wherein said housing of said spray tube (2) has a top part (6) having an essentially U-shaped cross section that is open at the bottom with flange faces (6c) projecting outward at the sides and having an essentially flat plate-shaped bottom part (7) whose outside longitudinal sections (7b) hold said flange faces (6c) of said top part (6) in a form-fitting manner.

10. Device according to claim 9, wherein outlet openings (3) are located in said bottom part (7).

* * * * *